United States Patent [19]

Soula

[11] Patent Number: 4,629,815

[45] Date of Patent: Dec. 16, 1986

[54] ISOMERIZATION/REARRANGEMENT OF POLYCHLOROBENZENES

[75] Inventor: Gérard Soula, Meyzieu, France

[73] Assignee: Rhone-Poulenc Industries, Paris, France

[21] Appl. No.: 276,481

[22] Filed: Jun. 23, 1981

[30] Foreign Application Priority Data

Jul. 1, 1980 [FR] France ............................. 80 14607
May 12, 1981 [FR] France ............................. 81 09392

[51] Int. Cl.⁴ ............................................. C07C 21/24
[52] U.S. Cl. .................................. 570/202; 564/504; 564/505
[58] Field of Search ................ 564/504, 505; 570/202

[56] References Cited

U.S. PATENT DOCUMENTS 2,355,337  8/1944  Spence ......................... 564/504 X
4,314,086  2/1982  Soula et al. ..................... 564/505 X

OTHER PUBLICATIONS

Bunnent et al., "Journal American Chemical Society", vol. 93, No. 5, pp. 1183–1205 (1971).
DiBiase et al., "Jour. Org. Chem.", vol. 43, No. 3, pp. 447–452 (1978).
Kontakte, pp. 11–31 and 36–48 (1977).

*Primary Examiner*—Robert V. Hines
*Attorney, Agent, or Firm*—Burns, Doane, Swecker & Mathis

[57] ABSTRACT

Polychlorobenzenes are isomerized/rearranged, by reacting (i) at least one tetrachlorobenzene, or at least one tetrachlorobenzene in admixture with at least one trichlorobenzene, pentachlorobenzene and/or hexachlorobenzene, or (ii) pentachlorobenzene, or pentachlorobenzene in admixture with at least one trichlorobenzene and/or hexachlorobenzene, or (iii) hexachlorobenzene, or hexachlorobenzene in admixture with at least one trichlorobenzene and/or dichlorobenzene, with at least one alkali metal amide, or at least one alkali metal alcoholate, or admixture thereof, said reaction being conducted in the presence of an agent which complexes the cation of the amide, alcoholate, or admixture thereof.

27 Claims, No Drawings

ISOMERIZATION/REARRANGEMENT OF POLYCHLOROBENZENES

BACKGROUND OF THE INVENTION

1. Field of the Invention

The present invention relates to the isomerization and/or rearrangement of polychlorobenzenes, and, more especially, to the preparation of polychlorobenzenes by rearrangement and/or isomerization of certain polychlorobenzenes congeneric thereto.

2. Description of the Prior Art

The isomerization/rearrangement of the polybromobenzenes is known to this art. Thus, J. F. Bunnett and Charles E. Moyer, Jr., *Journal of the American Chemical Society*, 93:5, pages 1183-1205 (Mar. 10, 1971), feature the reaction of sodium amide in liquid ammonia with 1,2,4-tribromobenzene. The latter compound rearranges into 1,3,5-tribromobenzene. A small amount of the di- and tetrabromo derivatives is also obtained. Similarly, the publication describes obtaining, from 1-iodo-2,4-dibromobenzene, a mixture containing the 1,3,5-isomer, together with 1,2,4-tribromobenzene, 1,3,5-tribromobenzene and 1-bromo-3,5-diiodobenzene. The article further describes the reaction of NaNH$_2$ in liquid ammonia with 1-bromo-2,4-dichlorobenzene, 1-iodo-4-bromochlorobenzene and 1-iodo-2,4,6-tribromobenzene.

The authors too have attempted to react, under the same conditions, the polychlorobenzenes (especially 1,2,4-trichlorobenzene). But this attempt was unsuccessful (page 1185, right-hand column).

SUMMARY OF THE INVENTION

Accordingly, a major object of the present invention is the provision of a novel process for the isomerization and/or rearrangement of the polychlorobenzenes, the subject process featuring reacting (1):

(i) at least one tetrachlorobenzene, optionally in admixture with at least one trichlorobenzene, and/or pentachlorobenzene, and/or hexachlorobenzene;

(ii) or pentachlorobenzene, optionally in admixture with at least one trichlorobenzene, and/or hexachlorobenzene;

(iii) or hexachlorobenzene in admixture with at least one trichlorobenzene, and/or dichlorobenzene, with (2), at least one alkali metal amide and/or at least one alkali metal alcoholate, in the presence of (3), at least one compound which complexes the cation of the amide and/or the alcoholate.

DETAILED DESCRIPTION OF THE INVENTION

More particularly according to this invention, in a first preferred embodiment thereof, the compound complexing the cation of the amide and/or the alcoholate is a tertiary amine sequestering agent having the structural formula:

$$N{+}CHR_1-CHR_2-O{+}CHR_3-CHR_4-O{)_n}R_5]_3 \quad [I]$$

wherein n is an integer greater than or equal to 0 and less than or equal to approximately 10 ($0 \leq n \leq 10$), $R_1$, $R_2$, $R_3$ and $R_4$, which may be the same or different, each represents a hydrogen atom or an alkyl radical having from 1 to 4 carbon atoms, and $R_5$ represents an alkyl or cycloalkyl radical having from 1 to 12 carbon atoms, a phenyl radical or a radical of the formula —$C_mH_{2m}$—O— 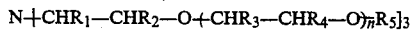 or $C_mH_{2m+1}$—O—, wherein m ranges from 1 to 12 ($1 \leq m \leq 12$), and O is phenyl.

In a second preferred embodiment of the invention, the complexing compound is a macrocyclic polyether having 15 to 30 ring carbon atoms and consisting of 4 to 10 —O—X units, wherein X is either —CHR$_6$—CHR$_7$— or, —CHR$_6$—CHR$_8$CR$_9$R$_7$—, with R$_6$, R$_7$, R$_8$ and R$_9$, which may be the same or different, each being a hydrogen atom or an alkyl radical having from 1 to 4 carbon atoms, and with one of the X's optionally being —CHR$_6$—CHR$_8$—CR$_9$R$_7$—, when the —O—X units comprise the —O—CHR$_6$—CHR$_7$— group.

According to a third preferred embodiment of the invention, the complexing compound is a macrocyclic compound or a bicyclic compound, having the general formulae [IIa] or [IIb]:

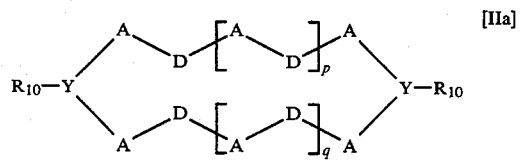

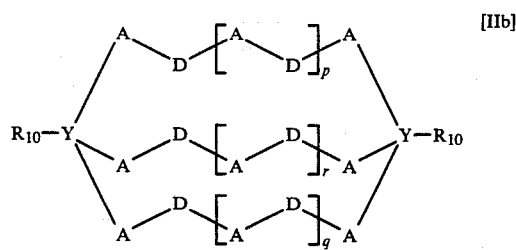

wherein:

(a) Y represents N or P;

(b) A represents an alkylene group having 1 to 3 carbon atoms; and (c) D represents O, S or N—R$_{11}$ wherein R$_{11}$ represents an alkyl radical having 1 to 6 carbon atoms, p, q and r, which may be the same or different, are integers ranging from 1 to 5.

And consistent with a fourth preferred embodiment of the invention, a mixture of at least two of the aforenoted specific complexing compounds are used.

The dichlorobenzene starting materials employed in the process according to the invention comprise 1,2-dichlorobenzene, 1,3-dichlorobenzene and 1,4-dichlorobenzene.

The trichlorobenzenes employed comprise 1,2,3-trichlorobenzene, 1,2,4-trichlorobenzene and 1,3,5-trichlorobenzene.

The tetrachlorobenzenes are 1,2,4,5-tetrachlorobenzene, 1,2,3,5-tetrachlorobenzene and 1,2,3,4-tetrachlorobenzene.

While not wishing to be bound to any particular theory, it would appear that the subject process is bottomed upon complexation of the complexation agent with the alkali metal amide and/or the alkali metal alcoholate, thus enabling the removal of a hydrogen atom from a polychlorobenzene, yielding a carbanion. As a result of the complexing of the alkali metal cation, the carbanion is soluble in the reaction medium, which in turn enables removal of a chlorine atom from another molecule of the polychlorobenzene, with this reaction proceeding in the same manner with the other species present in the reaction medium.

Thus, for example, when a pentachlorobenzene/1,2,4-trichlorobenzene admixture is employed, the amide or alcoholate anion effects removal of a hydrogen atom from the trichlorobenzene to yield the following three carbanions:

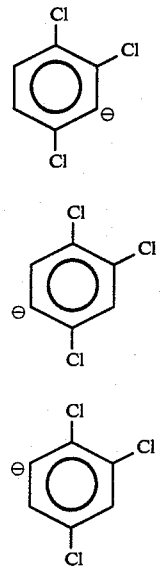

in varying proportions depending upon the acidity of the hydrogen atom removed. The (CI) carbanion will be present in major amount, but the (CIII) carbanion will be the most reactive in the subsequent stage of the removal of a chlorine atom from the pentachlorobenzene.

The action of the (CIII) carbanion on the pentachlorobenzene species principally results in the carbanion:

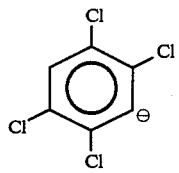

which in turn results from the removal of the chlorine from the pentachlorobenzene (other carbanions are formed by the removal of a chlorine atom from the other sites, but in lesser proportions) and the 1,2,3,5-tetrachloro derivative:

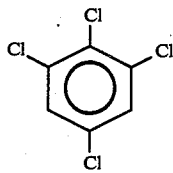

Thus, from a trichlorobenzene and a pentachlorobenzene, two tetrachlorobenzenes are obtained, according to the following reaction scheme:

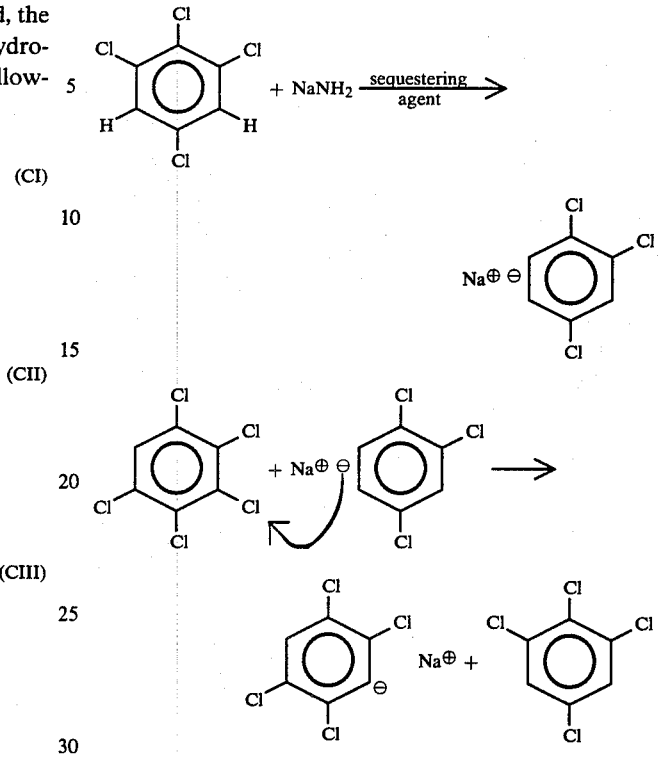

and the term "rearrangement" is used in this particular context.

On the other hand, 1,2,4-trichlorobenzene may be converted to 1,3,5-trichlorobenzene. When, under the conditions of the process of this invention, a tetrachlorobenzene (such as, for example, 1,2,4,5-tetrachlorobenzene) is mixed with 1,2,4-trichlorobenzene, the disappearance of the latter in favor of 1,2,5-trichlorobenzene is observed. Although it has not been clearly demonstrated, it appears that a molecule of tetrachlorobenzene loses a proton to yield a carbanion which in turn removes a chlorine atom from another molecule of tetrachlorobenzene, thus giving rise to a molecule of pentachlorobenzene and of 1,2,4-trichlorobenzene, i.e.:

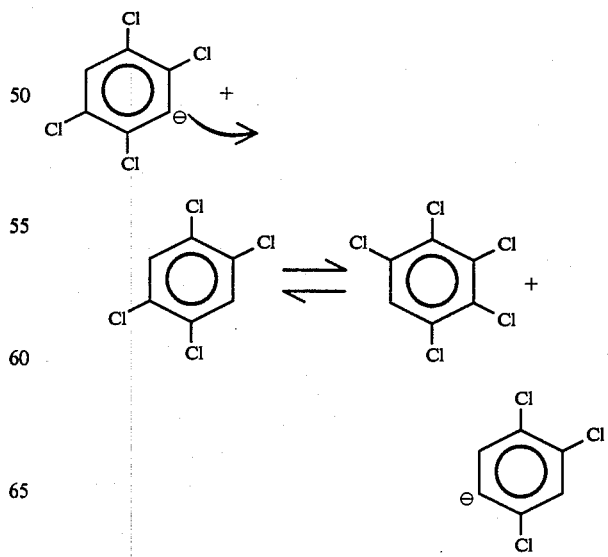

As hereinbefore mentioned, the reaction is reversible. But other reactions are also possible under these operating conditions, and first the appearance of 1,2,3,5-tetrachlorobenzene and then of 1,3,5-trichlorobenzene, are observed. The presence, in large amounts, of 1,2,4-trichlorobenzene favors its recombination with pentachlorobenzene, thereby reducing its concentration. The balance of the reaction then consists of an "isomerization" of 1,2,4-trichlorobenzene to 1,3,5-trichlorobenzene in the presence of tetrachlorobenzene, i.e.:

In the same manner, when, as the initial product, 1,2,3,4-tetrachlorobenzene is employed, a quasi-quantitative (on the order of 90%) transformation to the 1,2,3,5- and 1,2,4,5-isomers and to 1,2,4-trichloro- and 1,3,5-trichlorobenzene, and to pentachlorobenzene, is noted.

In a preferred embodiment of this invention, a tris-(oxaalkyl)-amine sequestering agent having the formula [I] is used, in which $R_1$, $R_2$, $R_3$ and $R_4$ represent a hydrogen atom or a methyl radical, with $R_5$ and n being as above-defined.

Among such tertiary amines, it is even more particularly preferred to use those in which n is greater than or equal to 0 and less than or equal to 6 and in which $R_5$ represents a hydrogen atom or an alkyl radical having from 1 to 4 carbon atoms.

Exemplary of such tris-(oxaalkyl)-amines [I] are:

[1] tris-(3-oxabutyl)-amine of the formula:

N$\pm$CH$_2$—CH$_2$—O—CH$_3$)$_3$

[2] tris-(3,6-dioxaheptyl)-amine of the formula:

N$\pm$CH$_2$—CH$_2$—O—CH$_2$—CH$_2$—O—CH$_3$)$_3$

[3] tris-(3,6,9-trioxadecyl)-amine of the formula:

N$\pm$CH$_2$—CH$_2$—O—CH$_2$—CH$_2$—O—CH$_2$—CH$_2$—O—CH$_3$)$_3$

[4] tris-(3,6-dioxaoctyl)-amine of the formula:

N$\pm$CH$_2$—CH$_2$—O—CH$_2$—CH$_2$—O—C$_2$H$_5$)$_3$

[5] tris-(3,6,9-trioxaundecyl)-amine of the formula:

N$\pm$CH$_2$—CH$_2$—O—CH$_2$—CH$_2$—O—CH$_2$—CH$_2$—O—C$_2$H$_5$)$_3$

[6] tris-(3,6-dioxanonyl)-amine of the formula:

N$\pm$CH$_2$—CH$_2$—O—CH$_2$—CH$_2$—O—C$_3$H$_7$)$_3$

[7] tris-(3,6,9-trioxadodecyl)-amine of the formula:

N$\pm$CH$_2$—CH$_2$—O—CH$_2$—CH$_2$—O—CH$_2$—CH$_2$—O—C$_3$H$_7$)$_3$

[8] tris-(3,6-dioxadecyl)-amine of the formula:

N$\pm$CH$_2$—CH$_2$—O—CH$_2$—CH$_2$—O—C$_4$H$_9$)$_3$

[9] tris-(3,6,9-trioxatridecyl)-amine of the formula:

N$\pm$CH$_2$—CH$_2$—O—CH$_2$—CH$_2$—O—CH$_2$—CH$_2$—O—C$_4$H$_9$)$_3$

[10] tris-(3,6-dioxa-4-methylheptyl)-amine of the formula:

N$\pm$CH$_2$—CH$_2$—O—CH(CH$_3$)—CH$_2$—O—CH$_3$)$_3$

[11] tris-(3,6-dioxa-2,4-dimethylheptyl)-amine of the formula:

N$\pm$CH$_2$—CH(CH$_3$)—O—CH(CH$_3$)—CH$_2$—O—CH$_3$)$_3$

[12] tris-(3,6,9,12-tetraoxatridecyl)-amine of the formula:

N$\pm$CH$_2$—CH$_2$—O$\pm$CH$_2$—CH$_2$—O)$_3$CH$_3$]$_3$ and

[13] tris-(3,6,9,12,15,18-hexaoxanonadecyl)-amine of the formula:

N$\pm$CH$_2$—CH$_2$—O$\pm$CH$_2$—CH$_2$—O)$_5$CH$_3$]$_3$.

The tris-(oxaalkyl)-amines [I] according to the invention are per se known to the prior art. Thus, French Pat. No. 1,302,365 describes the preparation of the tertiary amines N$\pm$CH$_2$—CH$_2$—O—CH$_3$)$_3$ and N$\pm$CH$_2$—CH$_2$—O—CH$_2$—CH$_2$—O—CH$_3$)$_3$ as by-products from the synthesis of the corresponding primary and secondary amines, such primary and secondary amines being valuable as intermediates in the synthesis of various pharmaceuticals, as corrosion inhibitors, as intermediates in the synthesis of agricultural chemicals, and as emulsifiers. It will also be appreciated, though, that the prior art, including the aforenoted French Pat. No. 1,302,365, is conspicuously devoid of any suggestion that the topic amines could be utilized in any reaction within the ambit of this invention. Such tris-(oxaalkyl)-amines [I] can also be prepared in two steps, by first reacting an alkali metal with an alkylene glycol monoether, and thence condensing the resulting salt with a tris-(haloalkyl)-amine.

The macrocyclic polyethers that too may be employed in the process of the invention are known generally as "crown ethers" and are described in published French Patent Application No. 2,026,481 (Application No. 69/43879).

The following are representative cyclic ethers of the immediately aforesaid genus:

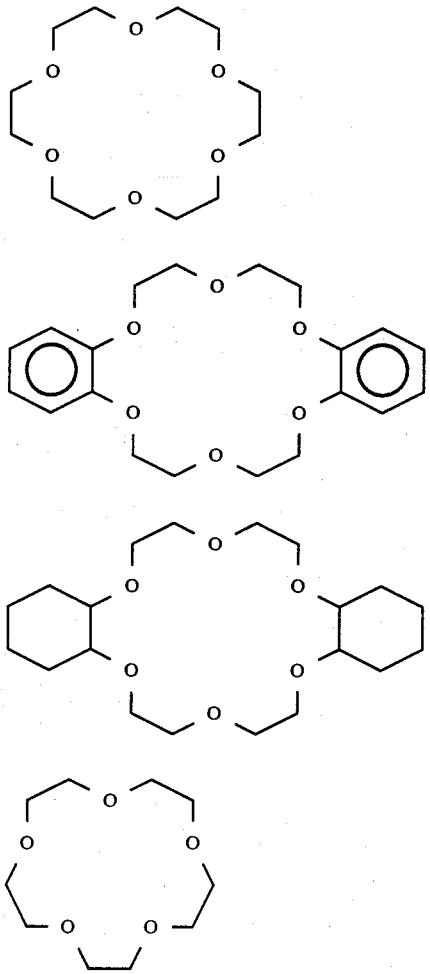

The macrocyclic or bicyclic compounds envisaged are described in published French Patent Application No. 2,052,947 (Application No. 70/21079). The following are exemplary of such macrocyclic or polycyclic compounds according to the invention:

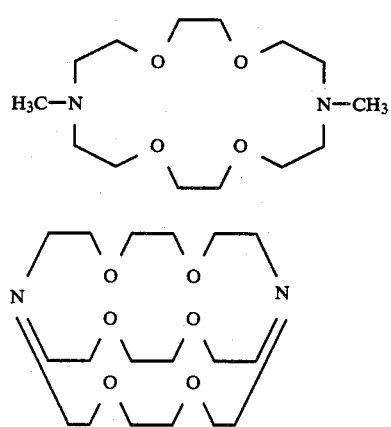

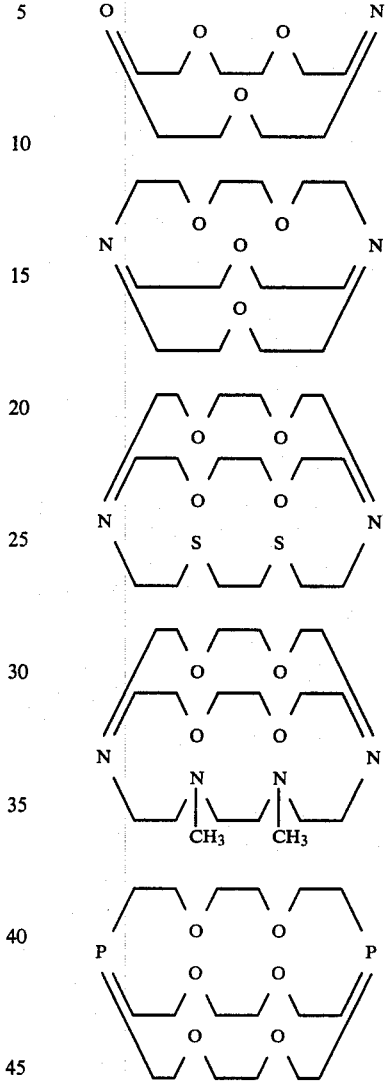

The process according to the invention may be carried out either in the presence or absence of a solvent. In the latter case, the starting material polychlorobenzene or polychlorobenzenes serve the function of the solvent. If an extraneous solvent be used, the same must satisfy a certain number of conditions: firstly, it must solubilize the sequestering agent (the latter is soluble in most of the typical solvents) and the polychlorobenzenes; it must also be chemically inert with respect to the polychlorobenzenes and the amides.

Preferably, an aromatic solvent, such as, for example, chlorobenzene, benzene or toluene, is selected.

The choice of the sequestering agent most suitable to be used in the process according to the invention is affected, inter alia, by taking into consideration the size of the alkali metal cation of the amide. The greater the size of the cation, the higher must be the number of oxygen atoms contained in the molecule of the sequestering agent.

The alkali metal amide or amides used in the process of the invention are advantageously selected from the group comprising $NaNH_2$, $KNH_2$, $LiNH_2$. Preferably, $NaNH_2$ is used.

The alkali metal alcoholate or alcoholates used in the process of the invention are advantageously selected from the group comprising the $RO^-M^+$ compounds, wherein $M^+$ preferably represents $Na^+$ and $K^+$ and R represents an alkyl radical preferably containing 1 to 6 carbon atoms. Exemplary of same are the sodium or potassium t-butylates.

The process according to the invention is preferably carried out at a temperature between $-20°$ C. and $60°$ C. Even more preferably, the reaction is conducted between $0°$ and $40°$ C.

The process is preferably conducted at atmospheric pressure. It should be understood, however, that pressures either higher or lower than atmospheric are also envisaged.

The sequestering agent is employed in amounts such that the molar ratio of the sequestering agent of Formula [I] to the alkali metal amide is preferably between 0.005 and approximately 0.5. Even more preferably, this ratio is between approximately 0.02 and approximately 0.2.

The molar ratio of the alkali metal amide or amides to the starting material polychlorobenzene or benzenes preferably is between approximately 1 and approximately 0.05. Even more preferably, it is between approximately 0.5 and approximately 0.05.

The proportions of the starting material polychlorobenzenes, when admixture of same is used, may vary between wide limits. These proportions are not critical with respect to the invention.

The process according to the invention is of particular interest for the preparation of 1,3,5-trichlorobenzene. In fact, 1,3,5-trichlorobenzene is a highly important intermediate in the synthesis of compounds having phytosanitary activity; it is obtained in the prior art by delicate and expensive processes, such as, for example, by the chlorination of 1-bromo-3,5-dichlorobenzene in the presence of an azobisnitrile compound or a benzoyl peroxide (Japanese Pat. No. 78. 18797).

The invention also has for its object an isomerization and/or rearrangement process such as defined hereinabove, for the preparation of 1,2,5-trichlorobenzene, characterized in that there are reacted at least one tetrachlorobenzene, optionally in admixture with 1,2,3-trichlorobenzene and/or 1,2,4-trichlorobenzene, and/or pentachlorobenzene, and/or hexachlorobenzene.

As would be apparent to one of skill in this art, the initial tetrachlorobenzene or benzenes may also be obtained, in situ, by the isomerization and/or rearrangement of yet other polychlorobenzenes.

More particularly consistent herewith, it is preferred to react at least one tetrachlorobenzene and 1,2,4-trichlorobenzene.

In effect, when using a single tetrachlorobenzene or a mixture of tetrachlorobenzenes, it has been found that 1,3,5-trichlorobenzene is formed in admixture with 1,2,4-trichlorobenzene and an equivalent amount of pentachlorobenzene. The pentachlorobenzene formed in this manner reacts with 1,2,4-trichlorobenzene to yield a mixture of tetrachlorobenzenes. The formation of pentachlorobenzene is restricted, while maintaining the production of 1,3,5-trichlorobenzene, by introducing 1,2,4-trichlorobenzene into the reaction medium.

In another embodiment of the invention, a mixture of 1,2,4,5-tetrachlorobenzene and 1,2,4-trichlorobenzene is used.

Preferably, 1,2,4,5-tetrachlorobenzene and 1,2,4-trichlorobenzene are used in amounts such that the molar ratio of the tetrachloro to the trichloro derivative is between approximately 0.1 and approximately 10.

A mixture of 1,2,4,5-tetrachloro- and 1,2,3,4,-tetrachlorobenzene, and 1,2,4-trichlorobenzene, may also be used.

The mixture of polychlorobenzenes obtained upon completion of the reaction is separated by means or methods well known to those skilled in this art, such as, for example, by distillation and/or fractionating crystallization.

The sequestering agent of Formula [I] used in the process according to the invention may also be prepared as described in the published French Patent Application No. 2,450,120.

In order to further illustrate the present invention and the advantages thereof, the following specific examples are given, it being understood that same are intended only as illustrative and in nowise limitative.

EXAMPLE 1

Into a 250 ml reactor equipped with a condenser and magnetic stirring means, there was introduced under a nitrogen (anhydrous) blanket, 0.1 mole, 1,2,4,5-tetrachlorobenzene (21.8 g), and the reaction mass adjusted to 100 g with anhydrous chlorobenzene. The mixture was agitated and cooled to $15°$ C. Subsequently, 0.005 mole tris-(3,6-dioxaheptyl)-amine (1.6 g), and 3.9 g of a mixture of sodium amide in toluene (50%–60%), or approximately 0.05 mole of sodium amide, were added thereto.

After one hour at $15°$ C., under agitation, the polychlorobenzene admixture consisted of:

| Polychlorobenzenes | Percentage |
|---|---|
| (i) 1,3,5-Trichlorobenzene | 12.8 |
| (ii) 1,2,4-Trichlorobenzene | 6.1 |
| (iii) 1,2,3,5-Tetrachlorobenzene | 36 |
| (iv) 1,2,4,5-Tetrachlorobenzene | 24 |
| (v) 1,2,3,4-Tetrachlorobenzene | 2.1 |
| (vi) Pentachlorobenzene | 15 |

EXAMPLE 2

Under the operating conditions employed in Example 1, there was introduced under nitrogen, 0.1 mole 1,2,3,4-tetrachlorobenzene (21.8 g), and the reaction mass adjusted to 100 g with anhydrous chlorobenzene. Subsequently, 0.005 mole tris-(3,6-dioxaheptyl)-amine (1.6 g), and 2 g sodium amide in solution in toluene, were added. An increase in temperature from $19°$ C. to $25°$ C. was noted. After 2 hours of reaction under agitation, the resultant composition of the polychlorobenzenes was as follows:

| Polychlorobenzenes | Percentage |
|---|---|
| (i) 1,3,5-Trichlorobenzene | 7 |
| (ii) 1,2,4-Trichlorobenzene | 15 |
| (iii) 1,2,4,5-Tetrachlorobenzene | 22.4 |
| (iv) 1,2,3,5-Tetrachlorobenzene | 33.6 |
| (v) 1,2,3,4-Tetrachlorobenzene | 6.3 |
| (vi) Pentachlorobenzene | 16 |

EXAMPLE 3

Utilizing the procedure of Example 2, the 1,2,3,4-tetrachlorobenzene was replaced by 1,2,3,5-tetrachlorobenzene. After 30 minutes of reaction, a mixture having the following composition was obtained:

| Polychlorobenzenes | Percentage |
| --- | --- |
| (i) 1,3,5-Trichlorobenzene | 14 |
| (ii) 1,2,4-Trichlorobenzene | 2 |
| (iii) 1,2,4,5-Tetrachlorobenzene | 21 |
| (iv) 1,2,3,5-Tetrachlorobenzene | 48 |
| (v) 1,2,3,4-Tetrachlorobenzene | 2 |
| (vi) Pentachlorobenzene | 13 |

It was possible to increase the content in 1,3,5-trichlorobenzene and to reduce the content in the pentachloro-derivative by adding 1,2,4-trichlorobenzene to the reaction mixture.

EXAMPLE 4

Into a 1-liter three-necked flask, equipped with a mechanical agitator inlet, 500 g anhydrous chlorobenzene, 108 g 1,2,4,5-tetrachlorobenzene (0.5 mole), 90.7 g 1,2,4-trichlorobenzene and 8 g tris-(3,6-dioxaheptyl)-amine, were successively introduced. The mixture was agitated and 20 g sodium amide, dissolved in 20 g toluene, were added thereto. The temerature of the mixture varied from 20° to 32° C. and after 2 hours of reaction, the composition of the polychlorobenzenes was as follows:

| Polychlorobenzenes | Percentage |
| --- | --- |
| (i) 1,3,5-Trichlorobenzene | 17 |
| (ii) 1,2,4-Trichlorobenzene | 36 |
| (iii) 1,2,4,5-Tetrachlorobenzene | 15 |
| (iv) 1,2,3,5-Tetrachlorobenzene | 23 |
| (v) 1,2,3,4-Tetrachlorobenzene | 5 |
| (vi) Pentachlorobenzene | 3 |

EXAMPLE 5

Under the operating conditions of Example 4, the tris-(3,6-dioxaheptyl)-amine was replaced by tris-(3,6-dioxanonyl)-amine. After 1 hour of reaction time, a mixture with the following composition was obtained:

| Polychlorobenzenes | Percentage |
| --- | --- |
| (i) 1,3,5-Trichlorobenzene | 16 |
| (ii) 1,2,4-Trichlorobenzene | 36 |
| (iii) 1,2,4,5-Tetrachlorobenzene | 15 |
| (iv) 1,2,3,5-Tetrachlorobenzene | 24 |
| (v) 1,2,3,4-Tetrachlorobenzene | 5 |
| (vi) Pentachlorobenzene | 3 |

EXAMPLE 6

Into a 250 ml reactor equipped with a condenser and magnetic stirring means, the following were introduced under nitrogen (anhydrous) atmosphere: 14.25 g hexachlorobenzene (0.05 mole), 29.4 g para-dichlorobenzene (0.2 mole), 55 g chlorobenzene, 1.6 g tris-(3,6-dioxaheptyl)-amine and 4.5 g sodium amide. After one hour at 20° C. under agitation, the polychlorobenzene mixture consisted of:

| Polychlorobenzenes | Percentage |
| --- | --- |
| (i) Paradichlorobenzene | 71.8 |
| (ii) 1,2,4-Trichlorobenzene | 0.2 |
| (iii) 1,2,4,5-Tetrachlorobenzene | 1.6 |
| (iv) 1,2,3,5-Tetrachlorobenzene | 2 |
| (v) 1,2,3,4-Tetrachlorobenzene | 0.4 |
| (vi) Pentachlorobenzene | 16 |
| (vii) Hexachlorobenzene | 8 |

EXAMPLE 7

Into a 250 ml reactor with a double jacket and with magnetic stirring means, there were introduced under nitrogen (anhydrous) atmosphere: 21.6 g 1,2,4,5-tetrachlorobenzene (0.1 mole), 18.15 g 1,2,4-trichlorobenzene (0.1 mole), 60 g chlorobenzene, 1.8 g tris-(3,6-dioxaoctyl)-amine (0.005 mole) and 3.9 g sodium amide (0.1 mole). After 1 hour, 30 minutes at 17° C. under agitation, the mixture of polychlorobenzenes consisted of:

| Polychlorobenzenes | Percentage |
| --- | --- |
| (i) 1,3,5-Trichlorobenzene | 8.3 |
| (ii) 1,2,4-Trichlorobenzene | 42.53 |
| (iii) 1,2,4,5-Tetrachlorobenzene | } 40.65 |
| (iv) 1,2,3,5-Tetrachlorobenzene | |
| (v) 1,2,3,4-Tetrachlorobenzene | 4.6 |
| (vi) Pentachlorobenzene | 3.9 |

EXAMPLE 8

Into a 150 ml reactor equipped with a condenser and with magnetic stirring means, there were introduced into nitrogen (anhydrous) atmosphere: 10.8 g 1,2,4,5-tetrachlorobenzene (0.05 mole) and 9 g 1,2,4-trichlorobenzene (0.05 mole), 30 g toluene, 0.8 g tris-(3,6-dioxaheptyl)-amine and 2 g sodium amide (0.05 mole). After one hour under agitation at 30° C., the polychlorobenzene mixture consisted of:

| Polychlorobenzenes | Percentage |
| --- | --- |
| (i) 1,3,5-Trichlorobenzene | 12.3 |
| (ii) 1,2,4-Trichlorobenzene | 43 |
| (iii) 1,2,4,5-Tetrachlorobenzene | 16 |
| (iv) 1,2,3,5-Tetrachlorobenzene | 23 |
| (v) 1,2,3,4-Tetrachlorobenzene | 3.8 |
| (vi) Pentachlorobenzene | 1.8 |

EXAMPLE 9

Into a 150 ml reactor equipped with a condenser and condenser vessel, there were introduced under nitrogen (anhydrous) atmosphere: 43.6 g 1,2,4,5-tetrachlorobenzene (0.2 mole), 9 g 1,2,4-trichlorobenzene (0.05 mole), 150 g chlorobenzene, 1.6 tris-(3,6-dioxaheptyl)-amine (0.005 mole) and 2 g sodium amide (0.05 mole).

After 30 minutes under agitation at 10° C., the composition of the mixture of polychlorobenzenes was:

| Polychlorobenzenes | Percentage |
| --- | --- |
| (i) 1,3,5-Trichlorobenzene | 10.6 |
| (ii) 1,2,4-Trichlorobenzene | 32 |
| (iii) 1,2,3,5-Tetrachlorobenzene | 19 |
| (iv) 1,2,4,5-Tetrachlorobenzene | 28 |
| (v) 1,2,3,4-Tetrachlorobenzene | 4.4 |

| Polychlorobenzenes | Percentage |
| --- | --- |
| (vi) Pentachlorobenzene | 6 |

EXAMPLE 10

Into a 50 ml reactor equipped with a condenser and with magnetic stirring means, there were introduced under nitrogen (anhydrous) blanket:

(1) 0.05 mole 1,2,4-trichlorobenzene (9.07 g);
(2) 0.02 mole 1,2,4,5-tetrachlorobenzene (4.3 g);
(3) 0.02 mole 1,2,3,5-tetrachlorobenzene (4.3 g); to which (4) 10 g anhydrous chlorobenzene were added.

This mixture was agitated at the ambient temperature of 18° C.

0.0025 mole (0.93 g) of the crown ether "dicyclohexyl 18 C-6" was added to the reaction mixture; same has the formula:

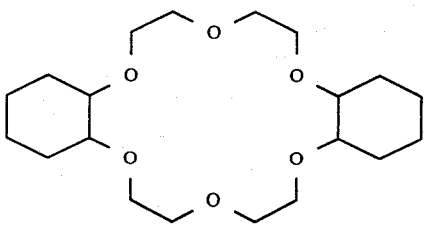

as was a mixture of sodium amide in toluene (50%-50%) with approximately 0.02 sodium amide.

An increase in temperature from 18° C. to 24° C. was detected.

After 4 hours of reaction under agitation, the polychlorobenzene mixture obtained consisted of:

| Polychlorobenzenes | Percentage |
| --- | --- |
| (i) 1,3,5-Trichlorobenzene | 14 |
| (ii) 1,2,4-Trichlorobenzene | 53 |
| (iii) 1,2,3,5-Tetrachlorobenzene } | 27.8 |
| (iv) 1,2,4,5-Tetrachlorobenzene | |
| (v) 1,2,3,4-Tetrachlorobenzene | 3.8 |
| (vi) Pentachlorobenzene | 1.1 |

EXAMPLE 11

Into a 50 ml reactor, equipped with a condenser and with magnetic stirring means, the following were introduced under nitrogen (anhydrous) atmosphere:

(1) 0.05 mole 1,2,4-trichlorobenzene (9.07 g);
(2) 0.04 mole 1,2,4,5-tetrachlorobenzene (8.6 g);

to which were subsequently added (3) 10 g anhydrous chlorobenzene.

The mixture was agitated at the ambient temperature of 19° C.

0.005 mole of a bicyclic compound having the following formula was then added thereto.

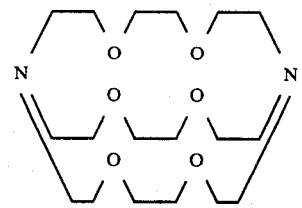

followed by the addition of a mixture of sodium amide in toluene (50%-50%), or approximately 0.02 mole sodium amide.

After 1 hour of reaction under agitation, the polychlorobenzene mixture obtained consisted of:

| Polychlorobenzenes | Percentage |
| --- | --- |
| (i) 1,3,5-Trichlorobenzene | 27.6 |
| (ii) 1,2,4-Trichlorobenzene | 36.8 |
| (iii) 1,2,3,5-Tetrachlorobenzene } | 31.3 |
| (iv) 1,2,4,5-Tetrachlorobenzene | |
| (v) 1,2,3,4-Tetrachlorobenzene | 2.7 |
| (vi) Pentachlorobenzene | 1.6 |

EXAMPLE 12

Into a 250 ml double jacketed reactor with magnetic stirring means, the following were introduced under nitrogen (anhydrous) atmosphere:

(1) 36.3 g 1,2,4-trichlorobenzene;
(2) 6.4 g tris-(3,6-dioxaheptyl)-amine;
(3) 6 g NaNH$_2$; and
(4) 16.2 g 1,2,4,5-tetrachlorobenzene.

A temperature of 17° C. was maintained for 2 hours.

The reaction mixture was then taken up in 200 ml water and 50 ml dichloromethane. The organic layer was then analyzed as follows:

| Polychlorobenzenes | Percentage |
| --- | --- |
| (i) 1,3,5-Trichlorobenzene | 32.6 |
| (ii) 1,2,4-Trichlorobenzene | 42.8 |
| (iii) 1,2,4,5-Tetrachlorobenzene | 17 |
| (iv) 1,2,3,5-Tetrachlorobenzene | 12.5 |
| (v) 1,2,3,4-Tetrachlorobenzene | 3 |
| (vi) Pentachlorobenzene | 2.1 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the isomerization/rearrangement of polychlorobenzenes, comprising reacting (i) at least one tetrachlorobenzene, or at least one tetrachlorobenzene in admixture with at least one trichlorobenzene, pentachlorobenzene and/or hexachlorobenzene, or (ii) pentachlorobenzene, or pentachlorobenzene in admixture with at least one trichlorobenzene and/or hexachlorobenzene, or (iii) hexachlorobenzene, or hexachlorobenzene in admixture with at least one trichlorobenzene and/or dichlorobenzene, with at least one alkali metal amide, or at least one alkali metal alcoholate, or admixture thereof, said reaction being conducted in the presence of an agent which complexes the cation of the amide, alcoholate, or admixture thereof.

2. The process as defined by claim 1, wherein the agent of complexation is a tertiary amine separating agent having the structural formula:

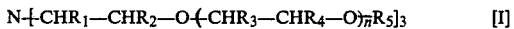

wherein n ranges from 0 to 10, $R_1$, $R_2$, $R_3$ and $R_4$, which may be the same or different, each represents a hydrogen atom or an alkyl radical having from 1 to 4 carbon atoms, and $R_5$ represents an alkyl or cycloalkyl radical having from 1 to 12 carbon atoms, a phenyl radical or a radical of the formula $-C_mH_{2m}-\phi$ or $C_mH_{2m+1}-\phi-$, wherein m ranges from 1 to 12 and $\phi$ is phenyl.

3. The process as defined by claim 2, wherein $R_1$, $R_2$, $R_3$ and $R_4$ are either hydrogen or methyl.

4. The process as defined by claim 3, wherein n ranges from 0 to 6, and $R_5$ is hydrogen or an alkyl radical having from 1 to 4 carbon atoms.

5. The process as defined by claim 2, said tertiary amine sequestering agent being selected from the group consisting of tris-(3-oxabutyl)-amine, tris-(3,6-dioxaheptyl)-amine, tris-(3,6,9-trioxadecyl)-amine, tris-(3,6-dioxaoctyl)-amine, tris-(3,6,9-trioxaundecyl)-amine, tris-(3,6-dioxanonyl)-amine, tris-(3,6,9-trioxadodecyl)-amine, tris-(3,6-dioxadecyl)-amine, tris-(3,6,9-trioxatridecyl)-amine, tris-(3,6-dioxa-4-methylheptyl)-amine, tris-(3,6-dioxa-2,4-dimethylheptyl)-amine, tris-(3,6,9,12-tetraoxatridecyl)-amine, and tris-(3,6,9,12,15,18-hexaoxanonadecyl)-amine.

6. The process as defined by claim 2, said tertiary amine sequestering agent being tris-(3,6-dioxaheptyl)-amine.

7. The process as defined by claim 2, said tertiary amine sequestering agent being tris-(3,6-dioxaoctyl)-amine.

8. The process as defined by claim 1, wherein the agent of complexation is a crown ether.

9. The process as defined by claim 1, wherein the agent of complexation is a macrocyclic polyether having 15 to 30 ring carbon atoms and comprising 4 to 10 —O—X units, wherein X is either —CHR$_6$—CHR$_7$— or —CHR$_6$—CHR$_8$CR$_9$R$_7$—, with R$_6$, R$_7$, R$_8$ and R$_9$, which may be the same or different, each being a hydrogen atom or an alkyl radical having from 1 to 4 carbon atoms.

10. The process as defined by claim 9, one X being —CHR$_6$—CHR$_8$—CR$_9$R$_7$ when the —O—X units comprise a —O—CHR$_6$—CHR$_7$— group.

11. The process as defined by claim 9, said macrocylic polyether being selected from the group consisting of those of the structural formulae:

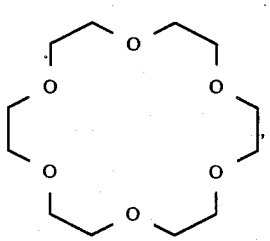

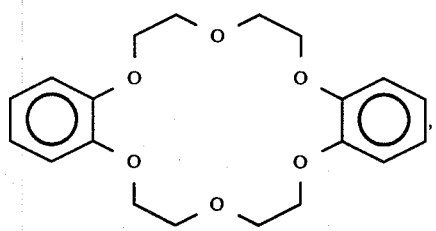

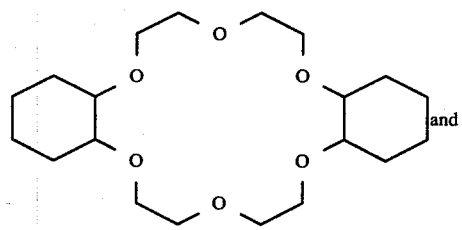

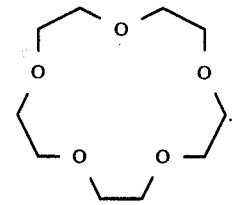

12. The process as defined by claim 1, wherein the agent of complexation is a macrocyclic/bicyclic compound having the structural formulae [IIa] or [IIb]:

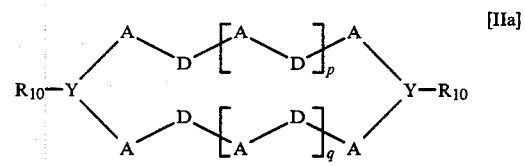

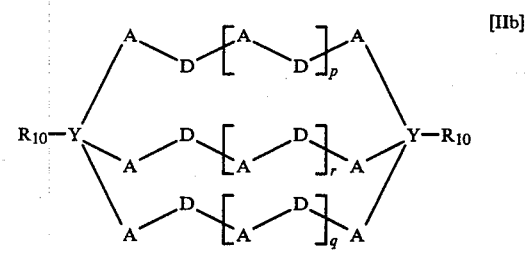

wherein Y represents N or P; A represents an alkylene group having 1 to 3 carbon atoms; and D represents O, S or N—R$_{11}$ wherein R$_{11}$ represents an alkyl radical having 1 to 6 carbon atoms; and p, q and r, which may be the same or different, are integers ranging from 1 to 5.

13. The process as defined by claim 12, said macrocyclic/bicyclic compound being selected from the group consisting of those of the structural formulae:

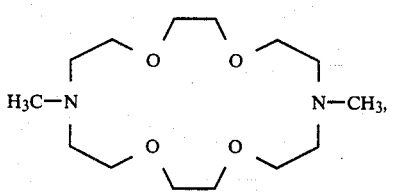

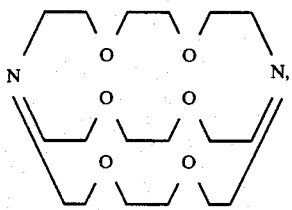

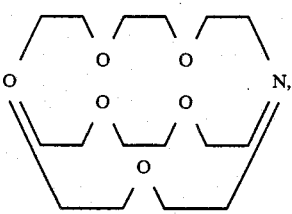

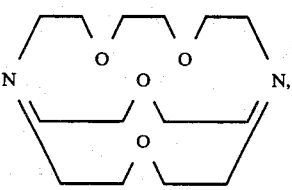

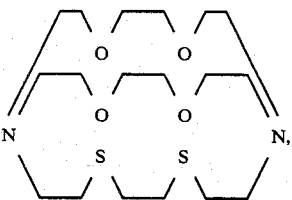

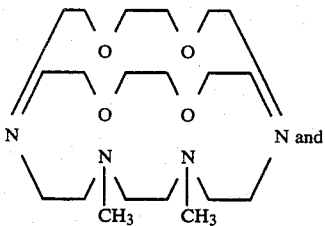

-continued

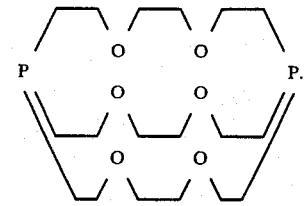

14. The process as defined by any of claims 1, 2, 8, 11, 12 or 13, the reaction being conducted in the presence of an aromatic solvent.

15. The process as defined by claim 14, said aromatic solvent being chlorobenzene, benzene or toluene.

16. The process as defined by any of claims 1, 2, 8, 11, 12 or 13, the reaction being with lithium, sodium or potassium amide.

17. The process as defined by any of claims 1, 2, 8, 11, 12 or 13, the reaction being with an alkali metal alcoholate of the formula $RO^-M^+$, wherein $M^+$ is sodium or potassium and R is an alkyl radical having from 1 to 6 carbon atoms.

18. The process as defined by claim 1, the reaction being conducted at a temperature of from about $-20°$ C. to $60°$ C.

19. The process as defined by claim 2, the reaction being with an alkali metal amide, and the molar ratio of amide to sequestering agent ranging from about 0.005 to 0.5.

20. The process as defined by claim 1, the reaction being with an alkali metal amide, and the molar ratio of amide to starting material polychlorobenzene ranging from about 1 to 0.05.

21. The process as defined by claim 1, comprising reacting the polychlorobenzene starting material (i).

22. The process as defined by claim 1, comprising reacting the polychlorobenzene starting material (ii).

23. The process as defined by claim 1, comprising reacting the polychlorobenzene starting material (iii).

24. The process as defined by claim 21, comprising the preparation of 1,2,5-trichlorobenzene by reacting the polychlorobenzene starting material, at least one tetrachlorobenzene, or at least one tetrachlorobenzene in admixture with 1,2,3-trichlorobenzene, 1,2,4-trichlorobenzene, pentachlorobenzene and/or hexachlorobenzene.

25. The process as defined by claim 24, comprising reacting at least one tetrachlorobenzene in admixture with 1,2,4-trichlorobenzene.

26. The process as defined by claim 24, comprising reacting 1,2,4,5-tetrachlorobenzene and 1,2,4-trichlorobenzene.

27. The process as defined by claims 25 or 26, the molar ratio of the tetrachlorobenzene to the trichlorobenzene ranging from about 0.1 to 10.

* * * * *